(12) United States Patent
Yan

(10) Patent No.: US 11,536,649 B1
(45) Date of Patent: Dec. 27, 2022

(54) URINAL ADDITIONAL DEVICE FOR DETECTING BLOOD IN URINE

(71) Applicant: TAIWAN REDEYE BIOMEDICAL INC., Hsinchu (TW)

(72) Inventor: Shuo-Ting Yan, Hsinchu (TW)

(73) Assignee: Taiwan Redeye Biomedical Inc., Hsinchu (TW)

(*) Notice: Subject to any disclaimer, the term of this patent is extended or adjusted under 35 U.S.C. 154(b) by 0 days.

(21) Appl. No.: 17/542,854

(22) Filed: Dec. 6, 2021

(51) Int. Cl.
| | |
|---|---|
| G01N 21/31 | (2006.01) |
| G01N 33/493 | (2006.01) |
| G06F 3/14 | (2006.01) |
| E03D 13/00 | (2006.01) |

(52) U.S. Cl.
CPC .......... *G01N 21/31* (2013.01); *E03D 13/005* (2013.01); *G01N 33/493* (2013.01); *G06F 3/14* (2013.01); *G01N 2201/0636* (2013.01)

(58) Field of Classification Search
CPC .. G01N 33/493; G01N 21/31; G01N 21/8507; E03D 13/005
See application file for complete search history.

(56) References Cited

U.S. PATENT DOCUMENTS

| | | | |
|---|---|---|---|
| 8,957,387 B2 * | 2/2015 | Sexton ............... | G01N 33/1886 250/373 |
| 10,761,015 B1 * | 9/2020 | Yan ...................... | G01N 33/721 |

FOREIGN PATENT DOCUMENTS

| | | |
|---|---|---|
| CN | 209941824 U | 1/2020 |
| TW | 201215748 A | 4/2012 |
| TW | I583952 B | 5/2017 |
| TW | 201727230 A | 8/2017 |
| TW | 202037899 A | 10/2020 |
| TW | 202139953 A | 11/2021 |

OTHER PUBLICATIONS

International Office Action Issued By Foreign Patent Office for Application No. 11120723240/110140674.

* cited by examiner

*Primary Examiner* — Maurice C Smith
(74) *Attorney, Agent, or Firm* — Rosenberg, Klein & Lee

(57) ABSTRACT

The present invention allows a sample urine to enter an entry hole formed on a shell and to flow through a flow pathway. A part of the sample urine remains in a groove of the flow pathway as collected urine. A measuring module in the shell includes a first side and a second side. The first side includes a light emitting unit and a light sensing unit. The second side includes a lens. The lens is mounted in the groove. The light emitting unit generates a detection beam. The detection beam passes the lens, the collected urine, a reflective mirror, the lens again, and into the light sensing unit. The light sensing unit receives the detection beam and generates a sensing signal. The processing unit generates a detection result signal according to the sensing signal, and a display unit immediately displays a test result of the sample urine.

17 Claims, 17 Drawing Sheets

URINAL ADDITIONAL DEVICE FOR DETECTING BLOOD IN URINE

BACKGROUND OF THE INVENTION

1. Field of the Invention

The present invention relates to a device for detecting blood in urine, more particularly a urinal additional device for detecting blood in urine.

2. Description of the Related Art

When a person is healthy, blood should not be present in the person's urine. When blood is found is a person's urine, or in other words when a person expels urine with blood, the person has some health issues. More particularly, the person with blood in urine might have major health issues such as endometrial/uterine cancer, bladder cancer, urinary tract stones, prostate cancer, or chronic kidney disease. For this reason, once blood is found present in a person's urine, the best option is to immediately seek medical attention for further checkups.

However, blood in urine is not very noticeable to naked human eyes. When concentration of blood cells is low, the person's urine might not be visibly red. For this reason, to find blood in urine, currently the urine must be first sampled, and then analyzed for contents.

An indicator of blood presence in the urine is to check if oxyhemoglobin is present in the urine. When oxyhemoglobin is present, blood is concluded to be present in urine. There are currently two ways to see whether oxyhemoglobin is present. One way is to hand over a urine sample to a hospital, and let the hospital use a centrifuge on the urine sample before investigating blood cells under a microscope. Though this process is precise and reliable, this process is however quite time consuming. As a result, this process fails to immediately tell the person whether there is blood present in his/her urine.

Another way is to dip the urine sample in a paper tester. A color of the paper tester will chemically change to other colors and show results of whether blood is present in the urine sample. However, rather than being a stable and reliable process, this process may be affected by qualities of the paper testers. The paper testers are prone to oxidization and moist, and such factors may affect a result of the paper tester. Furthermore, in this process, the person carrying out the test of dipping the urine sample to the paper tester might accidentally come into contact with the urine sample. In other words, this process is inconvenient and may cause some hygiene issues for the person carrying out the test.

Both processes mentioned above for testing blood in urine have disadvantages. Perhaps a new way of testing blood in urine is able to improve upon the aforementioned problems.

SUMMARY OF THE INVENTION

The present invention provides a urinal additional device for detecting blood in urine. By using the urinal additional device for detecting blood in urine, a person is able to immediately and reliably detect whether blood is present in the person's urine hygienically without contacting the urine.

The urinal additional device for detecting blood in urine includes a shell, a flow pathway, a display unit, a measuring module, a holder, and a processing unit.

The shell includes an entry hole and an exit hole. The entry hole is formed on a side surface of the shell, and the exit hole is formed on another side surface of the shell.

The flow pathway is formed within the shell and between the entry hole and the exit hole for communicating with the entry hole and the exit hole. The flow pathway includes a groove.

The display unit is mounted on the shell.

The measuring module is mounted inside the shell. The measuring module includes a first side and a second side. The first side includes a light emitting unit and a light sensing unit. The second side is opposite to the first side, and the second side includes a lens. The lens is mounted inside the groove.

The holder is attached to the second side of the measuring module. The holder includes a reflective mirror. The reflective mirror is mounted on the holder parallel to the lens.

The processing unit is mounted within the shell. The processing unit is electrically connected to the measuring module and the display unit.

When sample urine flows through the entry hole into the flow pathway and flows out of the exit hole, a part of the sample urine would remain in the groove of the flow pathway as collected urine. The light emitting unit generates a detection beam shooting towards the lens. The detection beam passes through the lens, passes through the collected urine, and shoots into the reflective mirror. Once reflected by the reflective mirror, the detection beam passes through the lens and shoots into the light sensing unit, and the light sensing unit correspondingly generates a sensing signal.

When the processing unit receives the sensing signal, the processing unit generates a detection result signal according to the sensing signal. The processing unit then sends the detection result signal to the display unit, and the display unit correspondingly displays a detection result of the sample urine.

By measuring absorption spectrum of the sample urine through the detection beam, contents of the sample urine are investigated, and whether oxyhemoglobin is present in the sample urine is known. The present invention detects whether blood is in the sample urine immediately and reliably. Furthermore, the flow pathway of the present invention allows the sample urine to flow freely into and out of the urinal additional device for detecting blood in urine, while leaving a part of the sample urine as the collected urine for blood in urine testing. This automatic process is more hygienic as it prevents a person from contacting the sample urine while carrying out the test.

DETAILED DESCRIPTION OF THE INVENTION

Figure 1:
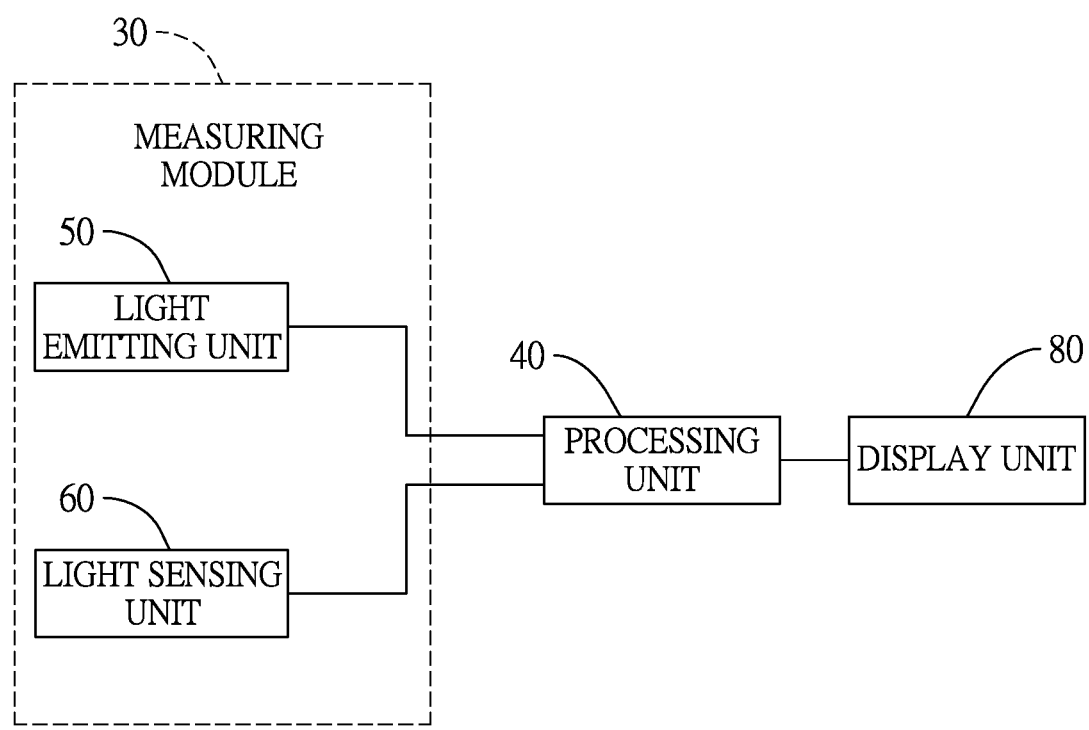
FIG. 1 is a block diagram of a urinal additional device for detecting blood in urine.
Figure 2:
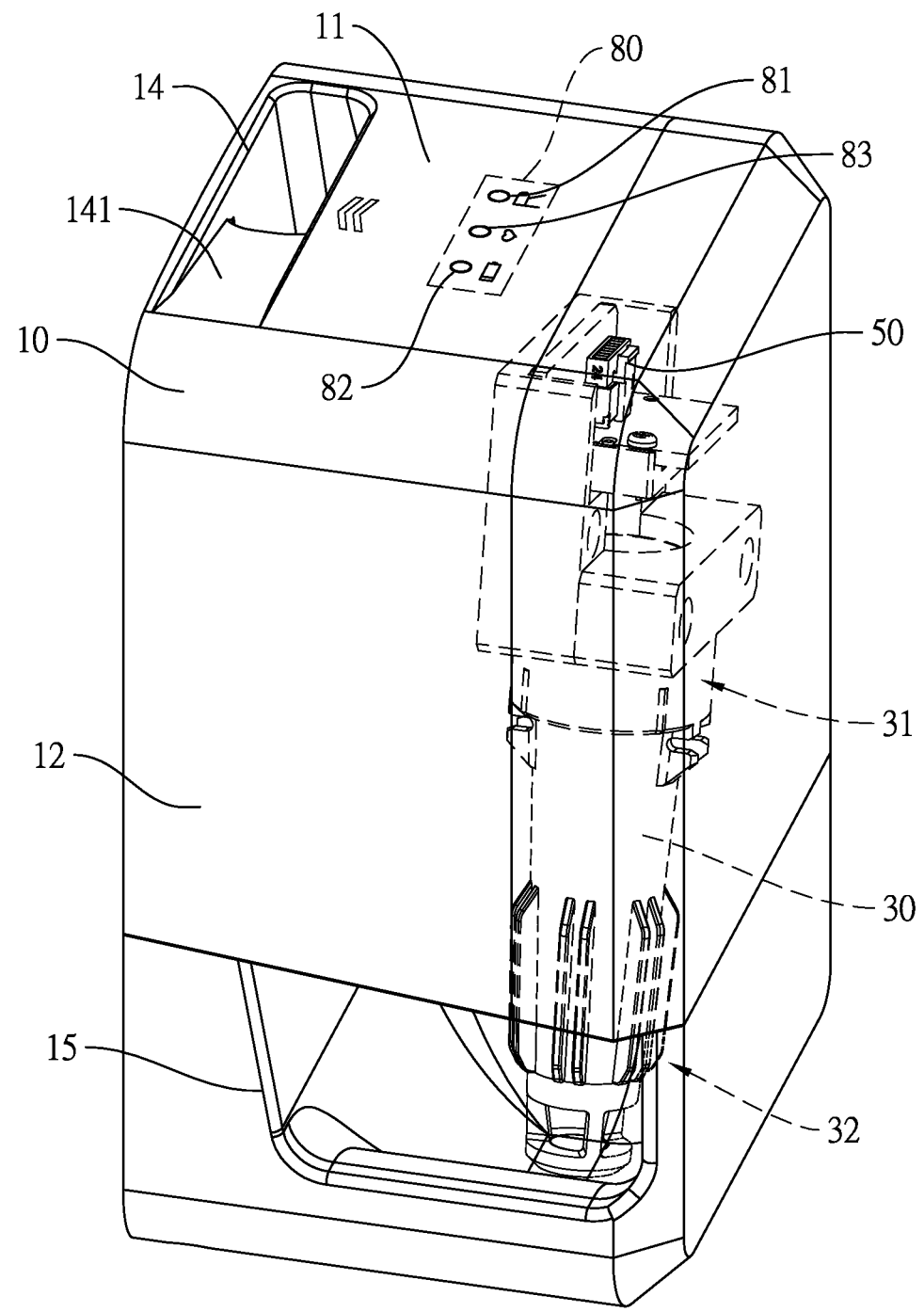
FIG. 2 is a perspective view of the urinal additional device for detecting blood in urine.
Figure 3:
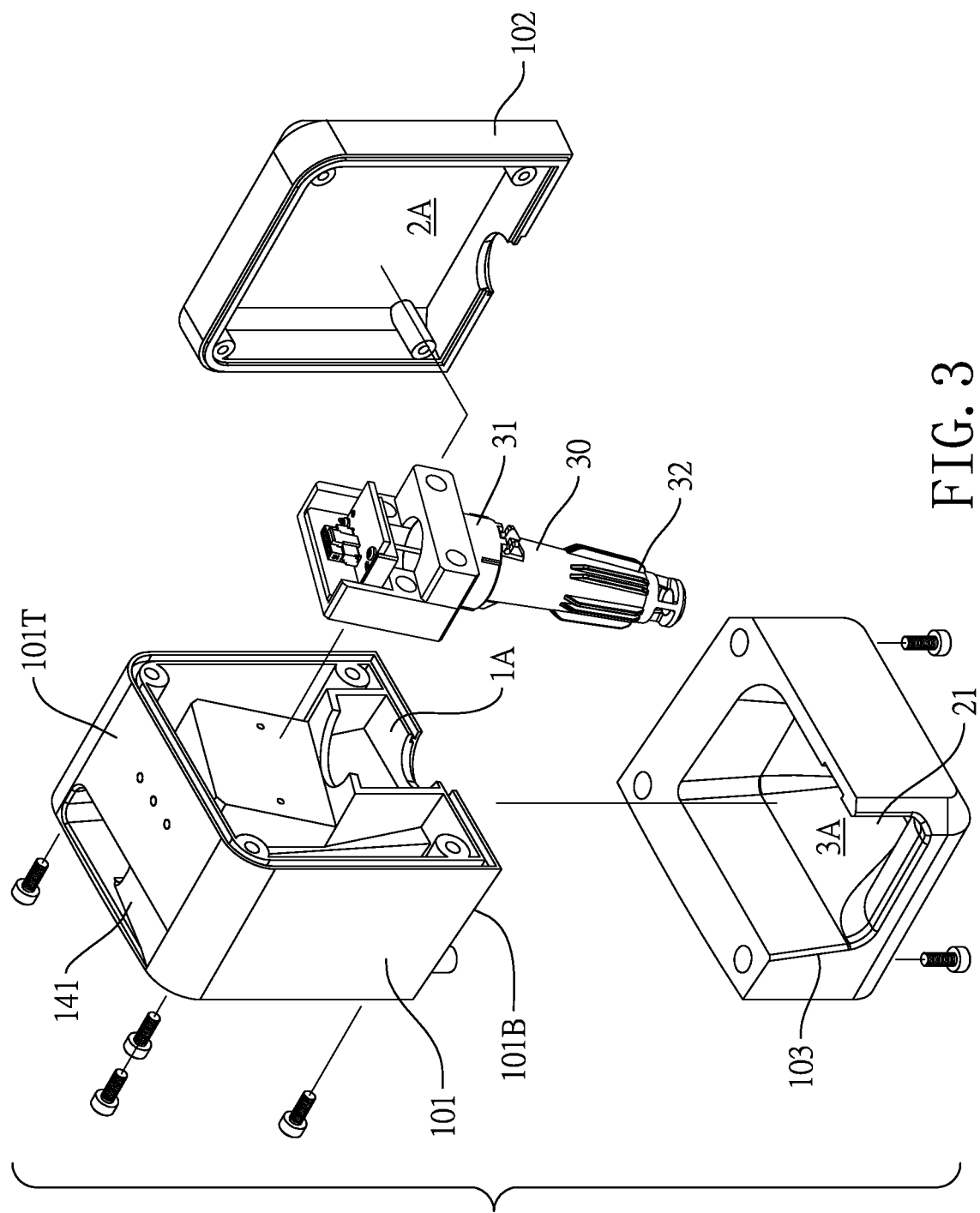
FIG. 3 is an exploded view of the urinal additional device for detecting blood in urine.
Figure 4:
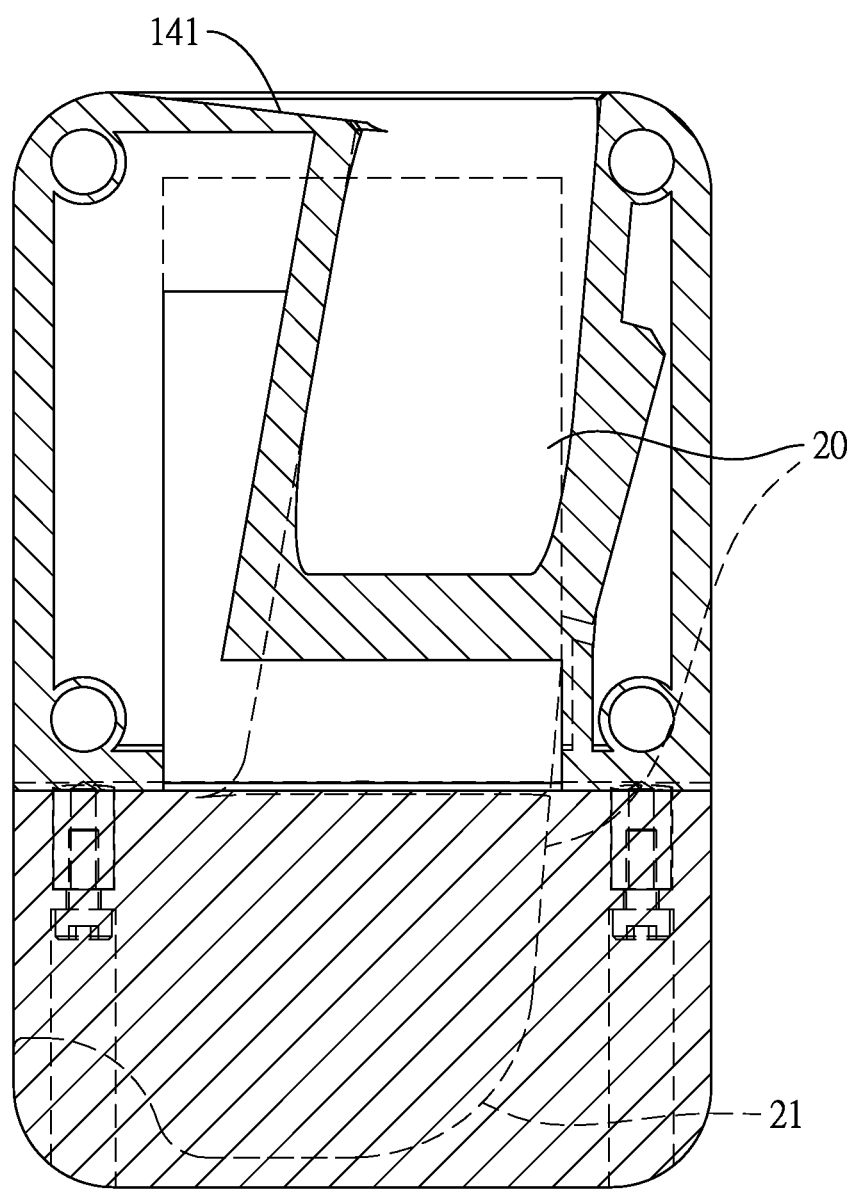
FIG. 4 is a cross-sectional view of the urinal additional device for detecting blood in urine.
Figure 5:
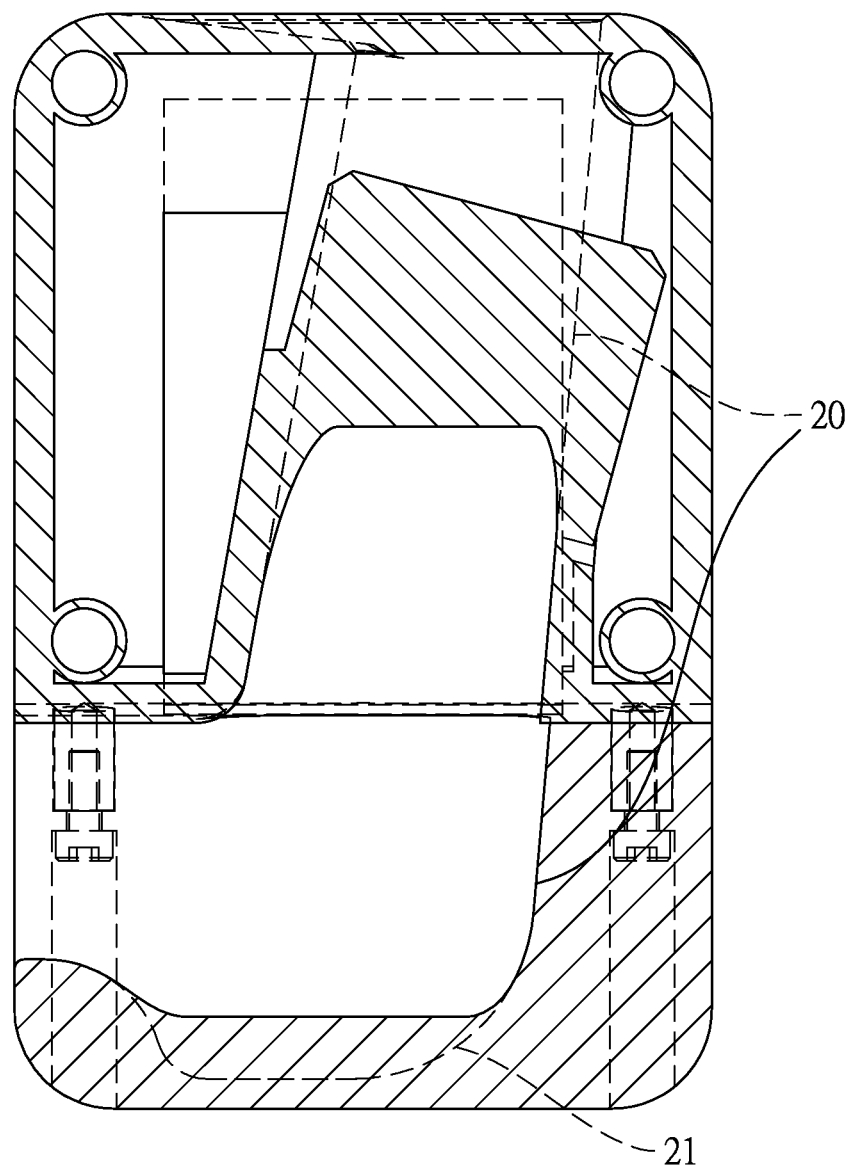
FIG. 5 is another cross-sectional view of the urinal additional device for detecting blood in urine.
Figure 6:
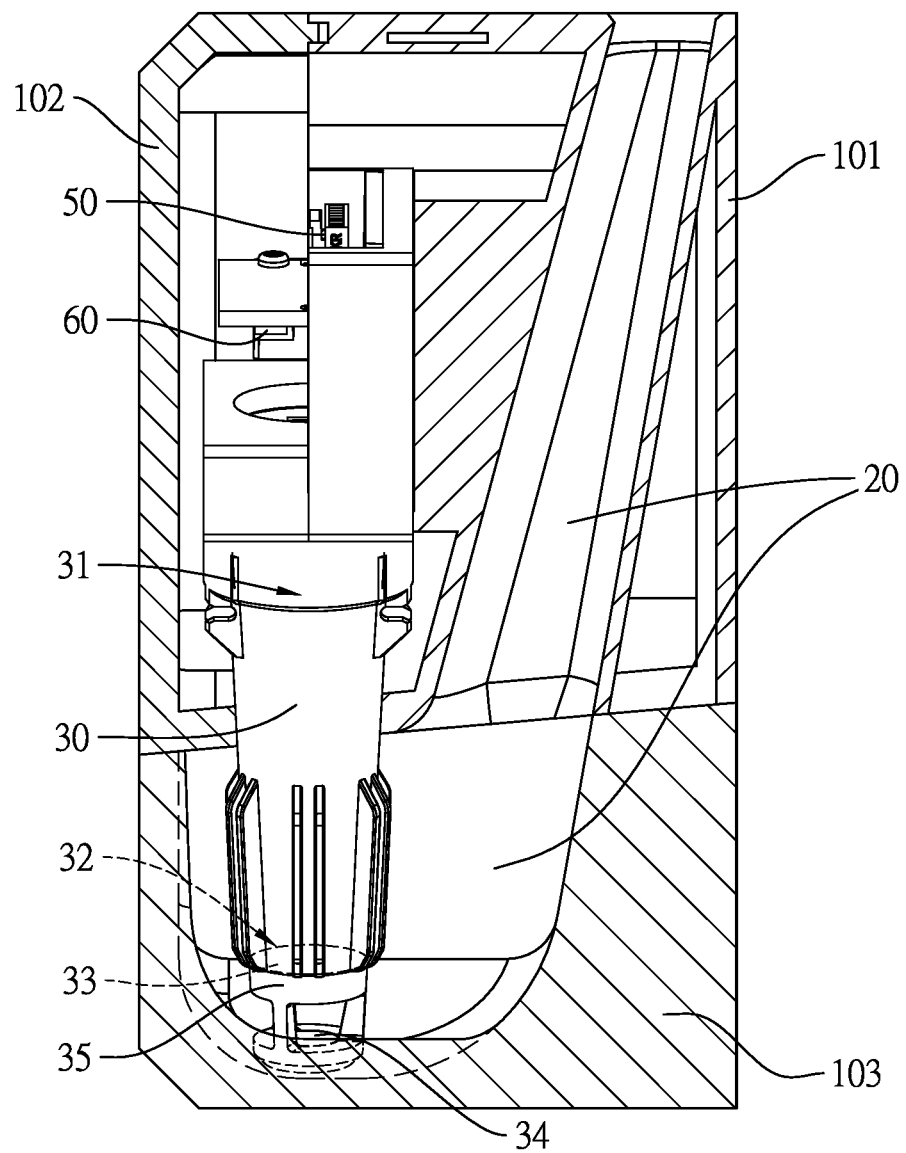
FIG. 6 is another cross-sectional view of the urinal additional device for detecting blood in urine.
Figure 7:
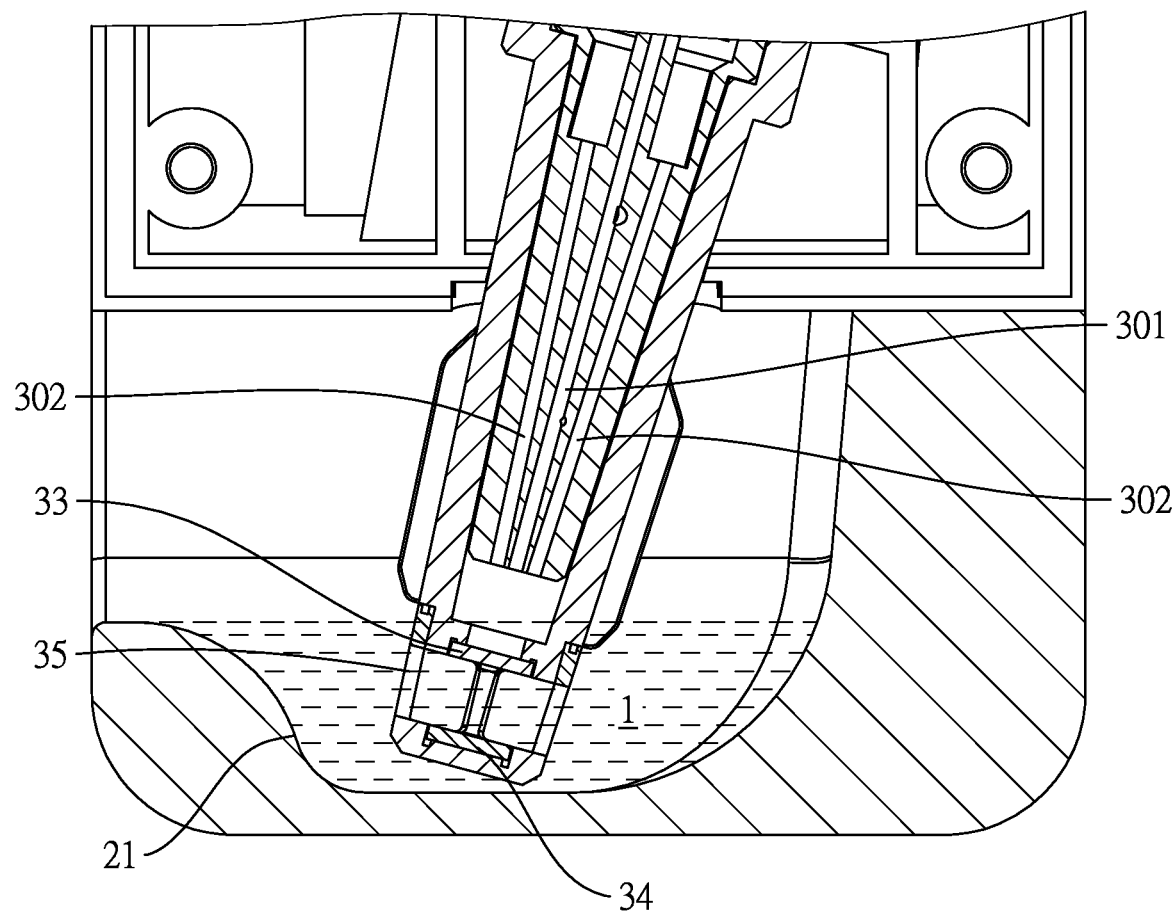
FIG. 7 is a cross-sectional view of detection of a collected urine of the urinal additional device for detecting blood in urine.

With reference to FIGS. 1 to 7, the present invention provides a urinal additional device for detecting blood in urine. The urinal additional device for detecting blood in urine includes a shell 10, a flow pathway 20, a measuring module 30, a holder 35, a processing unit 40, and a display unit 80.

The shell 10 includes a first side surface 11 and a second side surface 12. The first side surface 11 and the second side surface 12 are different side surfaces. An entry hole 14 is formed on the first side surface 11, and an exit hole 15 is formed on the second side surface 12.

The flow pathway 20 includes a groove 21. The flow pathway 20 is formed within the shell 10 and between the entry hole 14 and the exit hole 15 for communicating with the entry hole 14 and the exit hole 15. This way, when sample urine flows through the entry hole 14 and into the flow pathway 20, a part of the sample urine would remain in the groove 21 of the flow pathway 20, and other parts of the sample urine would flow out of the exiting hole 15. The part of the sample urine remaining in the groove 21 is collected urine 1, and the collected urine 1 would be used by the present invention for testing whether blood is present in urine.

The measuring module 30 is mounted inside the shell 10. The measuring module 30 includes a first side 31 and a second side 32. The first side 31 includes a light emitting unit 50 and a light sensing unit 60. The light emitting unit 50 and the light sensing unit 60 each aim at the second side 32 of the measuring module 30. The second side 32 is opposite to the first side 31, and the second side 32 includes a lens 33. The lens 33 seals an end of the second side 32 of the measuring module 30. The second side 32 of the measuring module 30 is placed inside the groove 21 of the flow pathway 20; in other words, the lens 33 of the second side 32 is also placed inside the groove 21. This means when the groove 21 is filled with the collected urine 1, the second side 32 is going to be soaked in the collected urine 1. The lens 33 would then prevent the collected urine 1 from flowing into the measuring module 30 as the lens 33 seals the second side 32.

The holder 35 is attached to the second side 32 of the measuring module 30. The holder 35 includes a reflective mirror 34. The reflective mirror 34 is mounted on the holder 35 parallel to the lens 33. The holder 35 is hollow, allowing the collected urine 1 to flow within the holder 35, and thus allowing the collected urine 1 to flow between the lens 33 and the reflective mirror 34.

The display unit 80 is mounted on the shell 10, and the processing unit 40 is mounted within the shell 10. The processing unit 40 is electrically connected to the display unit 80, and is also electrically connected to the measuring module 30, the light emitting unit 50, and the light sensing unit 60 within the shell 10.

The light emitting unit 50 generates a detection beam shooting towards the lens 33, and the light sensing unit 60 is responsible for sensing the detection beam. In other words, through the light emitting unit 50, the processing unit 40 generates the detection beam, and through the light sensing unit 60, the processing unit detects the detection beam. The detection beam shoots out from the lens 33 of the second side 32 and shoots into the collected urine 1 between the lens 33 and the reflective mirror 34. The detection beam then further shoots into the reflective mirror 34. Once reflected by the reflective mirror 34, the detection beam once again passes through the collected urine 1 and shoots into the lens 33 of the second side 32. The detection beam then further travels from the lens 33 of the second side 32 to the light sensing unit 60 on the first side 31. Upon receiving and sensing the detection beam, the light sensing unit 60 correspondingly generates a sensing signal. The light sensing unit 60 sends the sensing signal to the processing unit 40.

When the processing unit 40 receives the sensing signal, the processing unit 40 generates a detection result signal according to the sensing signal. The processing unit 40 then sends the detection result signal to the display unit 80, and the display unit 80 correspondingly displays a detection result of the sample urine. A light pathway of the detection beam is clear of contacting the light sensing unit 60 before contacting the reflective mirror 34. In other words, the light sensing unit 60 is clear of the light pathway of the detection beam detecting the collected urine 1.

In a first embodiment of the present invention, the processing unit 40 further stores a detection beam information and a light signal information. After the light sensing unit 60 generates the sensing signal, the light sensing unit 60 sends the sensing signal to the processing unit 40. The processing unit 40 analyzes a spectrum information of the sensing signal, and the processing unit 40 generates a detection result data according to the spectrum information and the detection beam information. The processing unit 40 further generates the detection result signal according to the detection result data and the light signal information. The processing unit 40 then sends the detection result signal to the display unit 80, and the display unit 80 correspondingly displays a detection result of the sample urine. The detection beam information stored in the processing unit 40 is a background spectrum information of the detection beam before the detection beam is altered by the sampled urine. In other words, the detection beam information excludes spectrum information of urine with blood.

With further reference to FIGS. 8 to 11, in the present embodiment, the display unit 80 further includes a result indicator 81, a low power indicator 82, and a sensory indicator 83. The result indicator 81, the low power indicator 82, and the sensory indicator 83 are each a light-emitting diode (LED). The result indicator 81 displays at least two colors of light according to the detection result signal, so as to display a test result of the sample urine. The present invention also includes a power unit 70. The power unit 70 is electrically connected to the processing unit 40, and the power unit 70 supplies electricity to the processing unit 40.

The processing unit 40 further stores an internal data. The internal data includes a thermistor threshold value and a low power threshold value. When the processing unit 40 detects a remaining power of the power unit 70 is less than the low power threshold value, the processing unit 40 generates a low on power signal. The processing unit 40 sends the low on power signal to the display unit 80, and the display unit 80 correspondingly displays a red light through the low power indictor 82. The red light is a warning message toward a user of the present invention. The warning message hints at the user to help replenish and restore electric power to the power unit 70.

Figure 8:
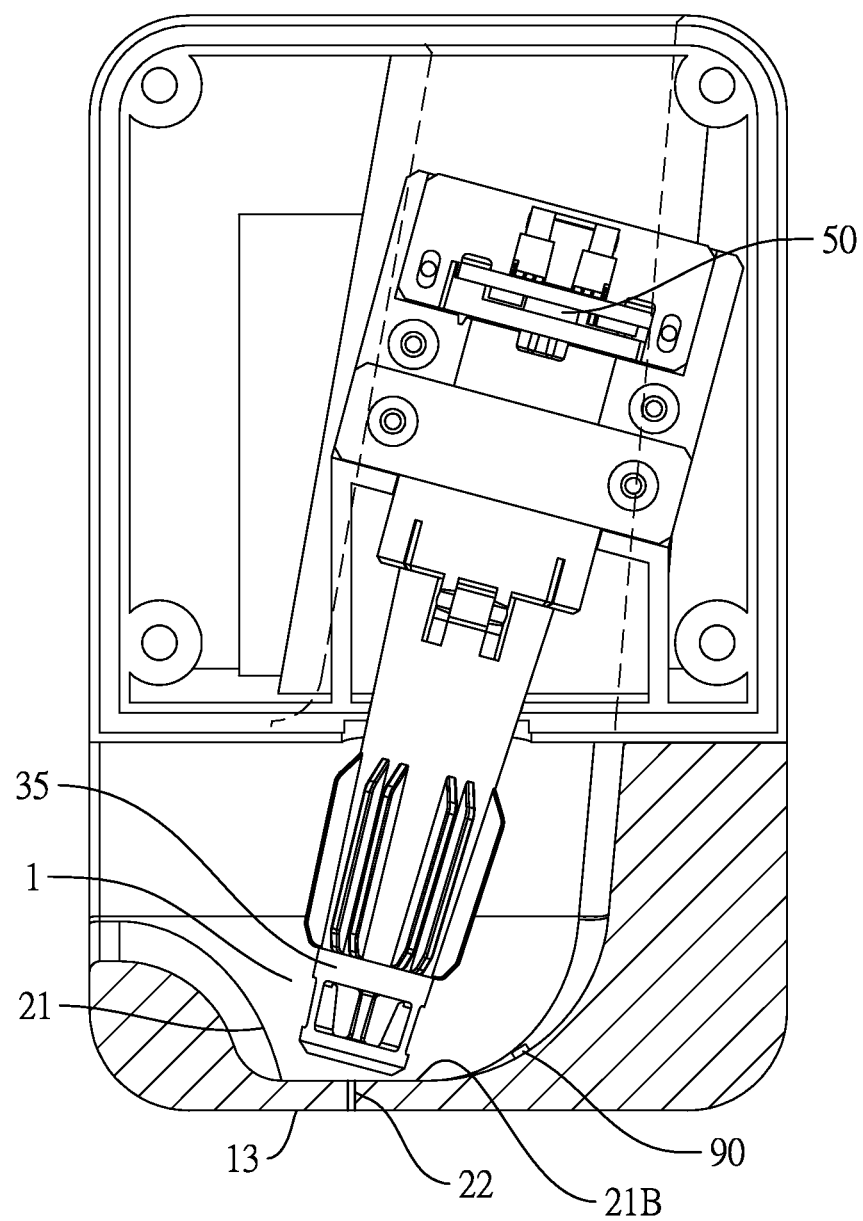
FIG. 8 is another cross-sectional view of the urinal additional device for detecting blood in urine.

The processing unit 40 is also electrically connected to a heat sensory unit 90. The heat sensory unit 90 includes a thermistor, and the heat sensory unit 90 is mounted inside the flow pathway 20 as shown in FIG. 8. The thermistor is a negative temperature coefficient thermistor (NTC thermistor), and the thermistor generates a thermistor signal and sends the thermistor signal to the processing unit 40. The NTC thermistor has properties such that the lower the temperature the NTC thermistor is exposed to, the higher resistance the NTC thermistor will have. Vice versa, the higher the temperature the NTC thermistor is exposed to, the lower resistance the NTC thermistor will have. Therefore under constant voltage, the higher the temperature the thermistor is exposed to, the more current would be able to flow through the thermistor.

When the sample urine enters through the entry hole 14 and flows through the flow pathway 20, the thermistor would be exposed to heat of the sample urine and have lower resistance. Vice versa, without contacting the sample urine, the thermistor would have lower temperature and higher resistance. When the thermistor has higher resistance, the processing unit 40 would stay and remain in a hibernation mode to conserve power usage. During the hibernation mode, the processing unit 40 is yet to initiate the light emitting unit 50 for generating the detection beam and is also yet to initiate the light sensing unit 60 for sensing the detection beam.

In the present embodiment, the light signal information stored in the processing unit 40 includes a first light signal, a second light signal, and a third light signal. According to changes in the thermistor signal, the processing unit 40 determines whether a resistance value of the heat sensory unit 90 is less than or equal to the thermistor threshold value. When the processing unit 40 determines the resistance value of the heat sensory unit 90 is less than or equal to the thermistor threshold value, the processing unit 40 generates a sensory indicator signal according to the light signal information. The processing unit 40 then sends the sensory indicator signal to the display unit 80, and the display unit 80 correspondingly displays the first light signal through the sensory indicator 83. When the sensory indicator 83 displays the first light signal, the sensory indicator 83 flashes a blue light three times. The flashing frequency of the blue light is comparable to a pulse frequency of an adult; in other words, the flashing frequency of the blue light is about 1 Hz to 1.5 Hz. This way, the sensory indicator 83 signals the user that the present invention has begun amassing the collected urine 1, and that the user should continue providing the sample urine through the entry hole 14.

The processing unit 40 further stores a pouring time information and a resting time information. The pouring time information includes a pouring time limit, and the resting time information includes a resting time limit. When the processing unit 40 generates the sensory indicator signal, the processing unit 40 also starts counting a waiting time. When the waiting time equals the pouring time limit, the processing unit 40 generates a stop pouring signal according to the light signal information. The processing unit 40 then sends the stop pouring signal to the display unit 80, and the display unit 80 correspondingly displays the second light signal through the sensory indicator 83. When the waiting time equals the resting time limit, the processing unit 40 stops counting the waiting time and generates a start measuring signal according to the light signal information. The processing unit 40 then sends the start measuring signal to the display unit 80, and the display unit 80 correspondingly displays the third light signal through the sensory indicator 83.

The second light signal and the third light signal are different light signals. The second light signal is aimed to tell the user that some time has passed after the pouring time limit, and that the collected urine 1 has been sufficiently collected. Therefore, the user should stop pouring the sample urine into the entry hole 14, and let the collected urine 1 settle down within the groove 21. The third light signal is aimed to tell the user that some more time has passed, and that the collected urine 1 inside the groove 21 has settled. Therefore, the present invention is ready to begin testing the sample urine for blood.

When the processing unit 40 starts generating the start measuring signal, the processing unit 40 ends the hibernation mode. Once the hibernation mode ends, the processing unit 40 only then starts controlling the light emitting unit 50 to generate the detection beam, and starts executing the aforementioned procedures to test the sample urine.

When the processing unit 40 just receives electricity from the power unit 70, in other words, when the power unit 70 re-supplies electricity to the processing unit 40 after battery changes, the processing unit 40 will generate a re-supplied signal. The processing unit 40 sends the re-supplied signal to the display unit 80, and the display unit 80 correspondingly flashes blue light twice through the sensory indicator 83. This tells the user that after electricity is re-supplied, the present invention has entered the hibernation mode successfully, and that the present invention will be waiting for the passage of the sample urine for exiting the hibernation mode.

Between the first side 31 and the second side 32 of the measuring module 30, the measuring module 30 further includes an emitting light optical channel 301 and at least one reflected light optical channel 302. The detection beam travels from the first side 31 of the measuring module 30 to the lens 33 of the second side 32 through the emitting light optical channel 301. Once reflected by the reflective mirror 34, the detection beam passes the lens 33 of the second side 32 and travels to the light sensing unit 60 on the first side 31 through the at least one reflected light optical channel 302.

Assuming the lens 33 is mounted on a second surface of the second side 32 of the measuring module 30, then opposite to the second surface would be a first surface located on the first side 31 of the measuring module 30. The first surface would contact the light sensing unit 60 on the first side 31. The aforementioned emitting light optical channel 301 and the at least one reflected light optical channel 302 are located between the first surface and the second surface. The normal line of the first surface is pointing at a first direction, and the first direction is also the direction the detection beam travels.

The emitting light optical channel 301 is formed at a center of the measuring module 30. The center of the measuring module 30 means between a center of cross-section of the first surface and a center of cross-section of the second surface. The emitting light optical channel 301 is located between the center of cross-section of the first surface and the center of cross-section of the second surface, and the emitting light optical channel 301 guides the detection beam to travel toward the first direction. The at least one reflected light optical channel 302 is formed outside of the emitting light optical channel 301. A first distance between the at least one reflected light optical channel 302 and the emitting light optical channel 301 on the first side is greater than a second distance between the at least one reflected light optical channel 302 and the emitting light optical channel 301 on the second side. In other words, the first distance of the emitting light optical channel 301 and the at least one reflected light optical channel 302 on the first surface is greater than the second distance of the emitting light optical channel 301 and the at least one reflected light optical channel 302 on the second surface. Furthermore, an outer diameter of the measuring module 30 on the first surface of the first side 31 is greater than the outer diameter of the measuring module 30 on the second surface of the second side 32. The above settlement follows how the detection beam disperses through traveling distance after reflected by the reflective mirror 34. This way the at least one reflected light optical channel 302 is able to guide the reflected detection beam to the light sensing unit 60 on the second surface.

The shell 10 further includes a first shell 101, a second shell 102, and a third shell 103. The shell 10 is a combination of the first shell 101, the second shell 102, and the third shell 103. The first shell 101 includes a chute 141, the entry hole 14, the flow pathway 20, and a first space 1A. The second shell 102 is mounted on a side of the first shell 101, wherein the side includes the first space 1A. The second shell 102 includes a second space 2A. The second space 2A communicates with the first space 1A, and the measuring module 30 is mounted between the first space 1A and the second space 2A. More particularly, once the first shell 101 is combined with the second shell 102, the first side 31 of the measuring module 30 is mounted inside a space formed by the first space 1A and the second space 2A.

The entry hole 14 is formed on a top surface 101T of the first shell 101, and the chute 141 is formed beside the entry hole 14. The chute 141 tilts from the top surface 101T of the first shell 101 towards the flowing channel 20, so as to more easily guide the sample urine to flow from the top surface 101T of the first shell 101 into the entry hole 14.

The third shell 103 is mounted on a bottom surface 101B of the first shell 101. The third shell 103 includes the exit hole 15 and a third space 3A. After the third shell 103 combines with the first shell 101, the second shell 102, and the measuring module 30, the third space 3A communicates with the flow pathway 20 of the first shell 101. Furthermore, the third space 3A of the third shell 103 includes the groove 21 of the flow pathway 20.

In the present embodiment, the present invention further includes a drain hole 22. The drain hole 22 is formed on a bottom wall 21B of the groove 21 of the flow pathway 20 as shown in FIG. 8. The drain hole 22 further forms through the bottom wall 21B of the groove 21 and an under surface 13 of the shell 10. In other words, the third shell 103 includes the drain hole 22, and the drain hole 22 forms through the bottom wall 21B of the groove 21 and the third shell 103. This way, when the user forgets to flush a urinal, the collected urine 1 in the groove 21 can be slowly drained through the drain hole 22, preventing a prolonged collection of the sample urine and corresponding hygienic issues. In normal cases, after the detection of blood in urine, the urinal in collaboration usage with the present invention should be flushed twice or thrice for maintaining hygiene by sufficiently flushing away the collected urine 1 in the groove 21 and the sample urine in the flow pathway 20.

Figure 9:
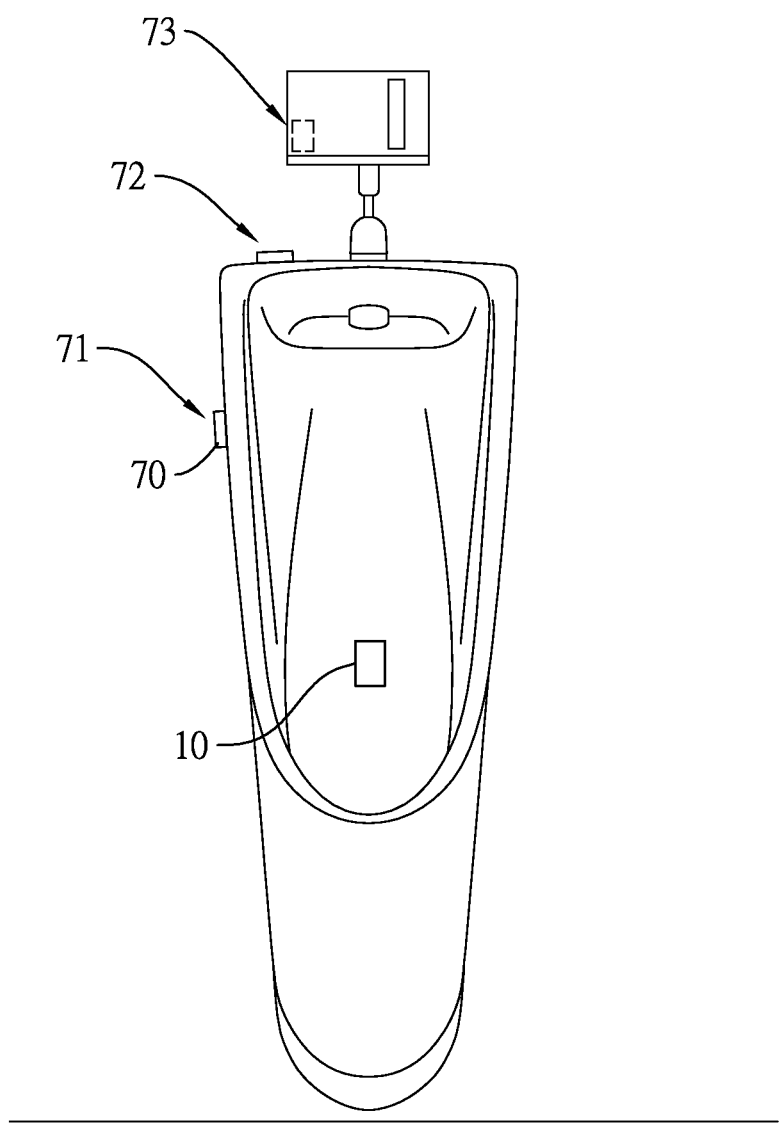
FIG. 9 is a perspective view of how the urinal additional device for detecting blood in urine is applied to a urinal.
Figure 10:
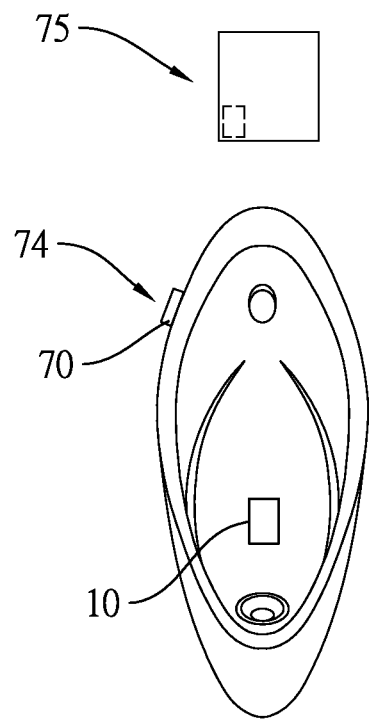
FIG. 10 is a perspective view of how the urinal additional device for detecting blood in urine is applied to another urinal.
Figure 11:
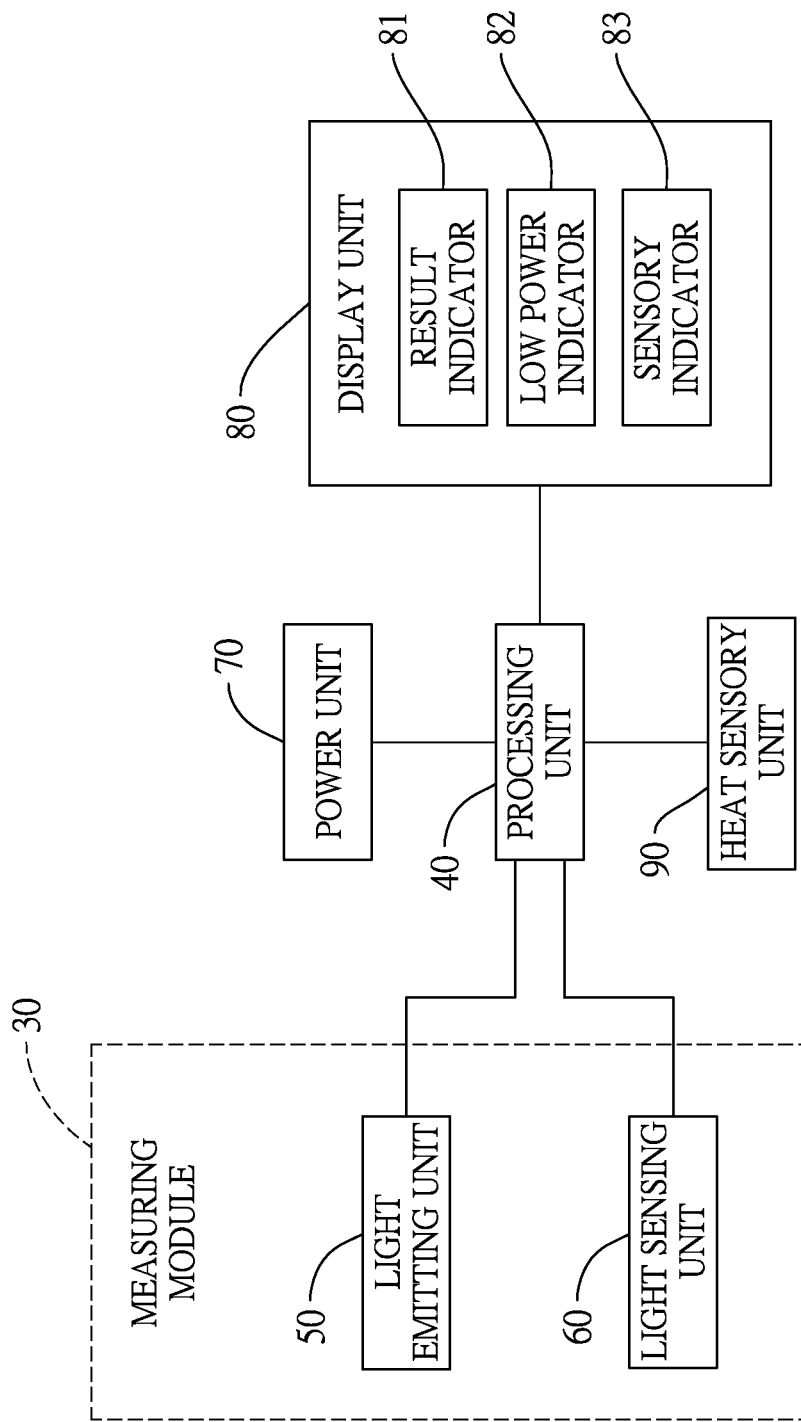
FIG. 11 is another block diagram of the urinal additional device for detecting blood in urine.

In the present embodiment, the power unit 70 uses batteries for supplying electricity to the processing unit 40. More particularly, the power unit 70 uses four triple A (3A) batteries for supplying electricity of 6 volts (V). With reference to FIGS. 9 and 10, the power unit 70 may be installed in different locations around the urinal. FIG. 9 details a urinal wherein a controller of the urinal is inside a box. In FIG. 9, the power unit 70 may be installed on a side of the urinal, as shown in a first position 71, or on top of the urinal, as shown in a second position 72, or inside the box, as shown in a third position 73. In FIG. 10, another type of urinal is shown, wherein the controller of the urinal is installed inside of a wall. In FIG. 10, the power unit 70 may be installed on a side of the urinal, as shown in a fourth position 74, or inside the wall with the controller of the urinal, as shown in a fifth position 75.

Both FIGS. 9 and 10 detail how the present invention is combined with a urinal, in other words, how the present invention transforms a urinal into a testing device. The shell 10 of the urinal additional device for detecting blood in urine is mounted in the middle of the urinal, ensuring maximum collection of the sample urine. The entry hole 14 is placed facing away from the ground and closely along the wall of the urinal. This way the sample urine would enter the entry hole 14 flowing along the wall of the urinal due to gravitational force. The exit hole 15 is free to face any direction, as long as the sample urine is able to flow out freely.

The power unit 70 further includes a direct current (DC) to DC converter. The DC to DC converter increases the voltage from 6 V to higher voltages for the processing unit 40. The power unit 70 is electrically connected to the processing unit 40 inside the shell 10 via a cable. The light sensing unit 60 is a light sensing panel. The light sensing panel includes multiple photo detectors (PDs). The processing unit 40 is a processor, and the light emitting unit 50 includes multiple LEDs. The thermistor threshold value being considered by the processing unit 40 corresponds to a resistance value of the NTC thermistor at 40 Celsius (° C.). A distance between the lens 33 and the reflective mirror 34 is 5 millimeters (mm). A distance traveled by the detection beam inside of the collected urine 1 is around 10 mm.

The present invention uses absorption spectrum to determine whether blood is present in the sample urine. Since the detection beam is able to immediately and reliably provide absorption spectrum information, and since the processing unit 40 only requires a few seconds to analyze test data, the present invention is able to accurately provide the test result within a few seconds, hence providing a better way to measure blood in urine than aforementioned procedures in prior arts. A detailed description of how the present invention uses the absorption spectrum to determine whether blood is present in the sample urine will be described in later parts.

Figure 12:
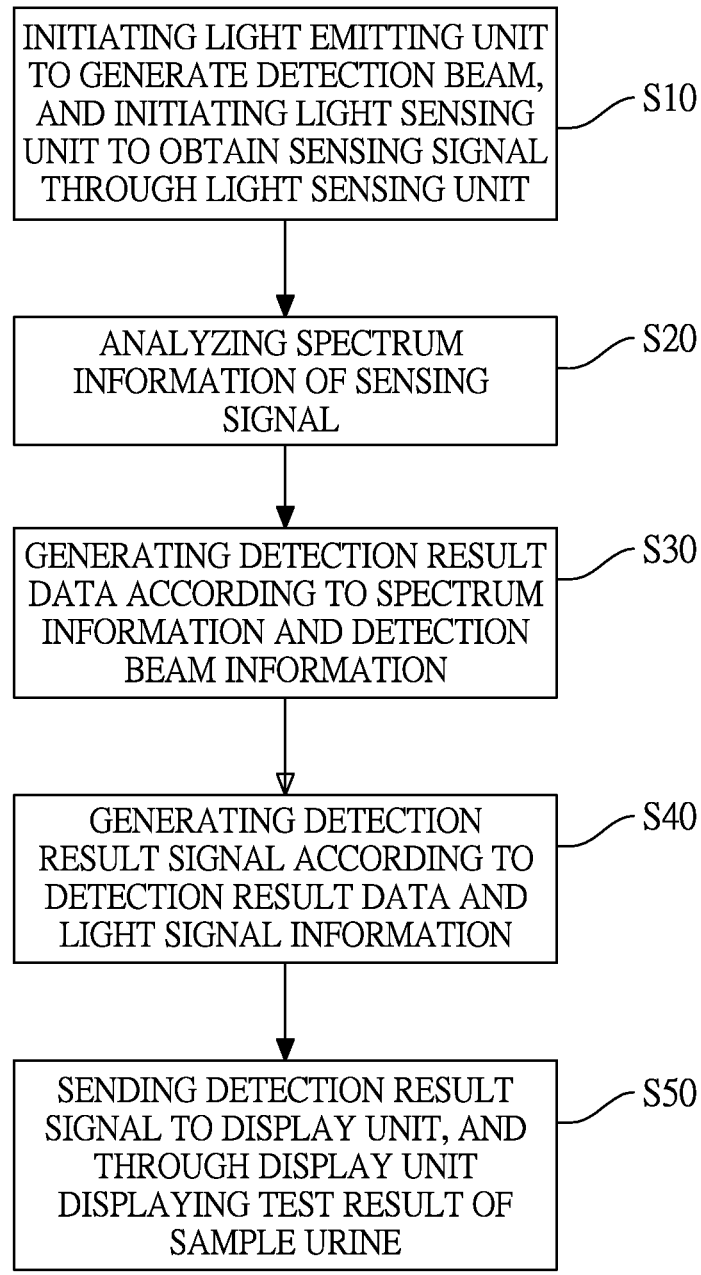
FIG. 12 is a flow chart of how the urinal additional device for detecting blood in urine functions.

With reference to FIG. 12, FIG. 12 details a flow chart of how the urinal additional device for detecting blood in urine functions. The following steps describing how the present invention functions are executed by the processing unit 40. The following steps include:

Step S10: initiating the light emitting unit 50 to generate the detection beam, and initiating the light sensing unit 60 to obtain the sensing signal through the light sensing unit 60.

Step S20: analyzing the spectrum information of the sensing signal.

Step S30: generating the detection result data according to the spectrum information and the detection beam information.

Step S40: generating the detection result signal according to the detection result data and the light signal information.

Step S50: sending the detection result signal to the display unit 80, and through the display unit 80 displaying the test result of the sample urine.

Figure 13:
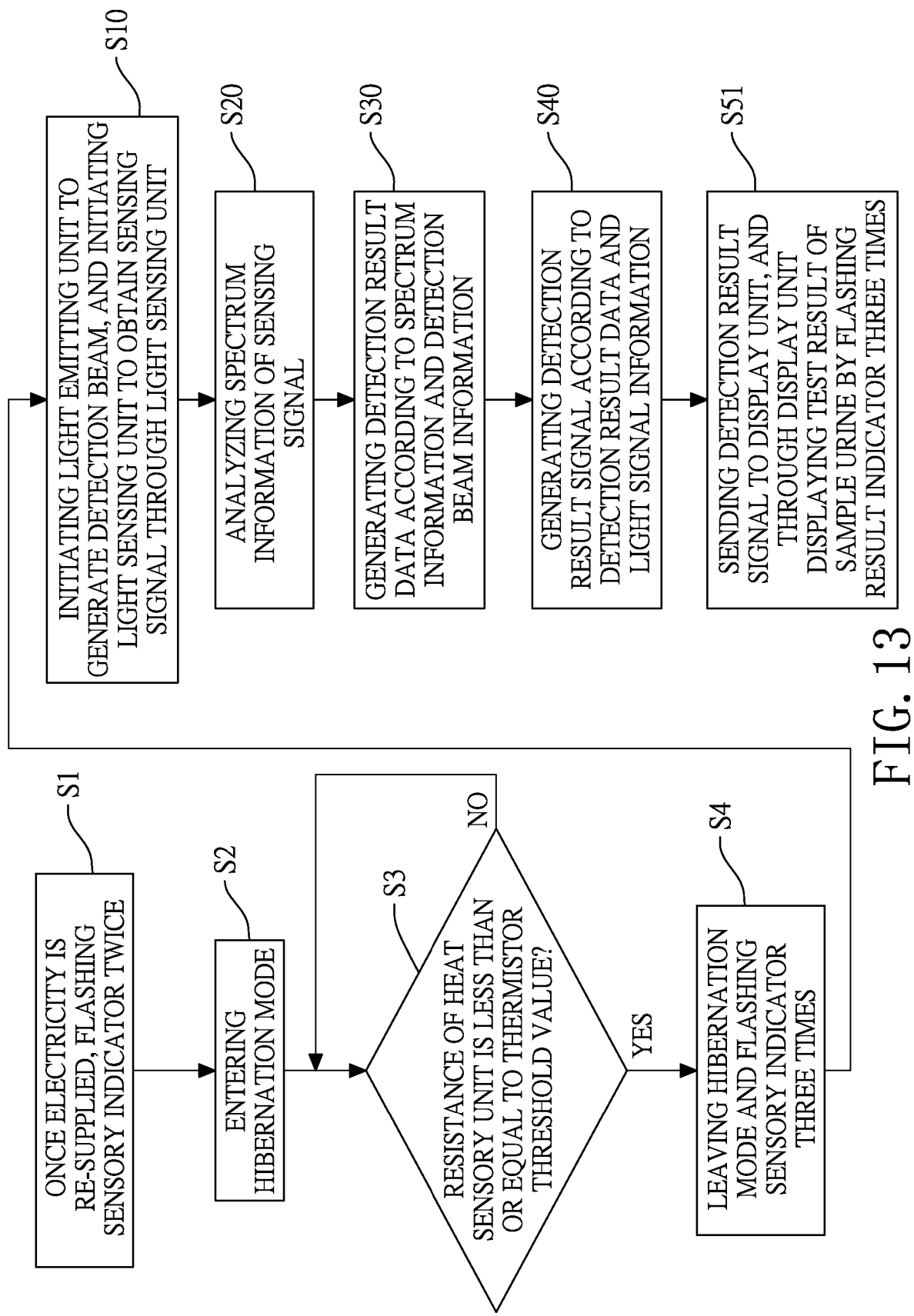
FIG. 13 is another flow chart of how the urinal additional device for detecting blood in urine functions.

With reference to FIG. 13, in the present embodiment, the present invention further includes the following steps:

Step S1: when detecting the power unit 70 just re-supplied electricity, generating the re-supplied signal, sending the re-supplied signal to the display unit 80, and through the display unit 80 flashing the sensory indicator 83 twice.

Step S2: entering hibernation mode.

Step S3: determining whether the resistance of the heat sensory unit 90 is less than or equal to the thermistor threshold value.

When determining the resistance of the heat sensory unit 90 is greater than the thermistor threshold value, staying in hibernation mode and re-executing step S3 to re-determine whether the resistance of the heat sensory unit 90 is less than or equal to the thermistor threshold value.

Step S4: when determining the resistance of the heat sensory unit 90 is less than or equal to the thermistor threshold value, leaving the hibernation mode, through the display unit 80 flashing the sensory indicator 83 three times, and executing step S10.

In another embodiment, after executing step S40, instead of executing S50, the processing unit 40 executes a modified step as the following:

Step S51: sending the detection result signal to the display unit 80, and through the display unit 80 displaying the test result of the sample urine by flashing the result indicator 81 three times.

Figure 14:
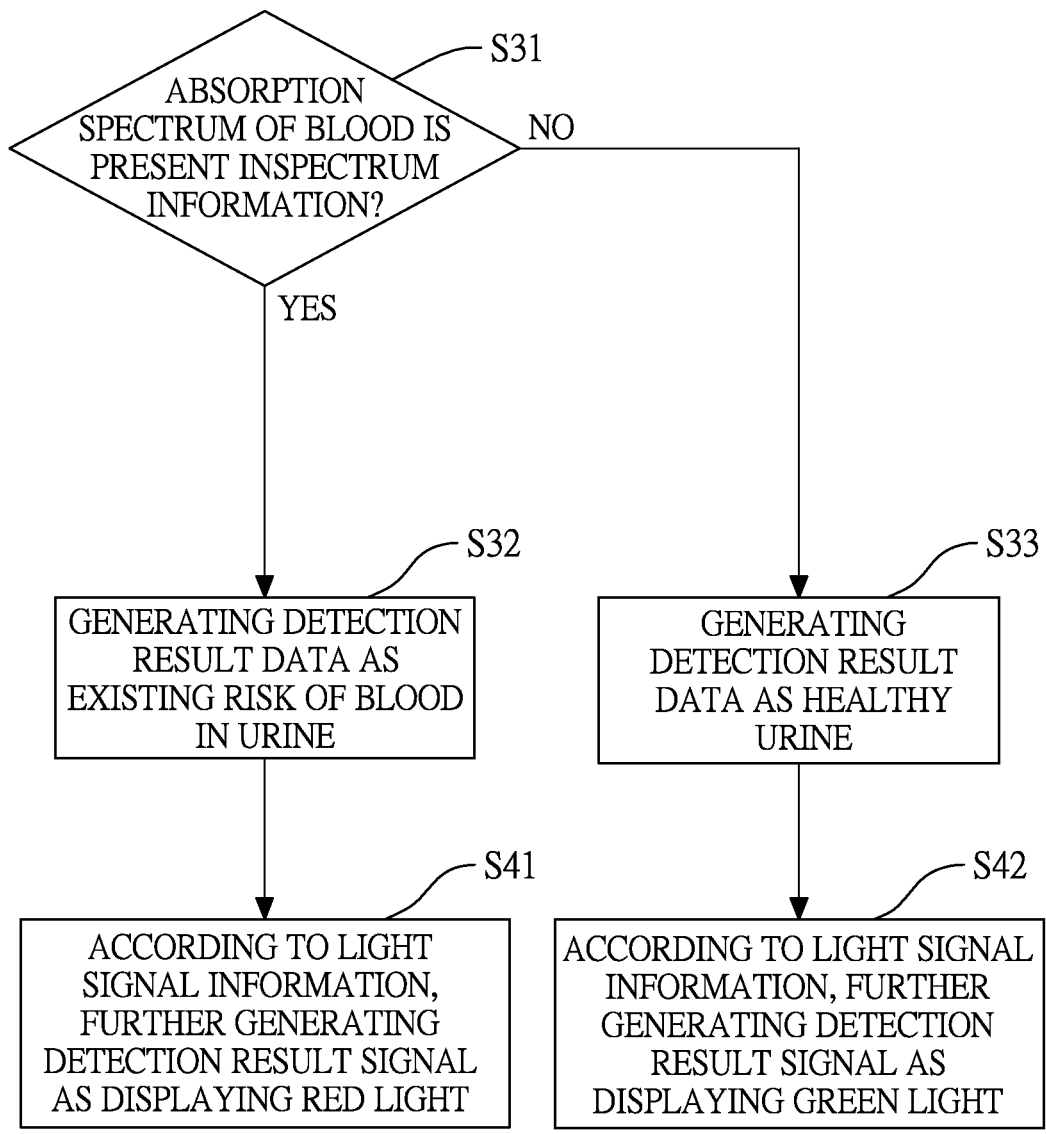
FIG. 14 is a flow chart of how an embodiment of the urinal additional device for detecting blood in urine functions.

With reference to FIG. 14, in the present embodiment, step S30 further includes the following sub-steps:

Step S31: determining whether absorption spectrum of blood is present in the spectrum information.

Step S32: when determining absorption spectrum of blood is present in the spectrum information, generating the detection result data as existing risk of blood in urine.

Step S33: when determining absorption spectrum of blood is absent in the spectrum information, generating the detection result data as healthy urine.

Furthermore, step S40 further includes the following sub-steps:

Step S41: after generating the detection result data as existing risk of blood in urine, according to the light signal information, further generating the detection result signal as displaying red light.

Step S42: after generating the detection result data as healthy urine, according to the light signal information, further generating the detection result signal as displaying green light.

This way, the user will be able to immediately know whether blood is present in the sample urine through the display unit 80. When the display unit 80 receives the detection result signal as displaying red light, the display unit 80 accordingly displays red light to the user, signaling the user blood is most likely present in the sample urine. When the display unit 80 receives the detection result signal as displaying green light, the display unit 80 accordingly displays green light to the user, signaling the user the sample urine is normal without traces of blood.

Figure 15:
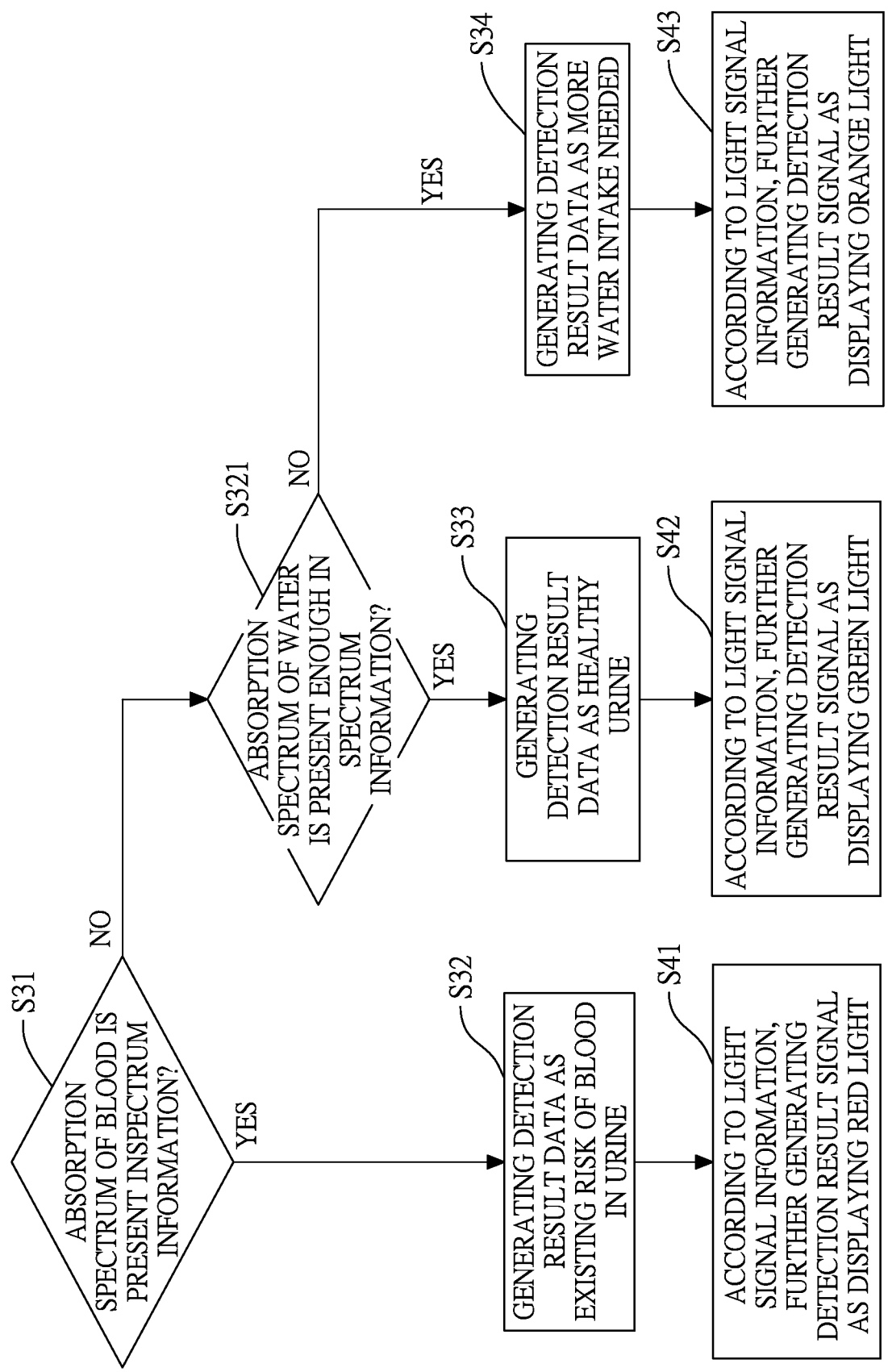
FIG. 15 is a flow chart of how another embodiment of the urinal additional device for detecting blood in urine functions.

With reference to FIG. 15, in another embodiment of the present invention, within step S30, and more particularly after step S31 and before step S33, further includes the following sub-steps:

Step S321: when determining absorption spectrum of blood is absent in the spectrum information, further determining whether absorption spectrum of water is present enough in the spectrum information.

When determining absorption spectrum of water is present enough in the spectrum information, executing step S33.

Step S34: when determining absorption spectrum of water is absent enough in the spectrum information, generating the detection result data as more water intake needed.

Furthermore, step S40 includes the following sub-steps:

Step S43: after generating the detection result data as more water intake needed, according to the light signal information, further generating the detection result signal as displaying orange light.

This way, after finding out blood is absent in the sample urine, the present invention further determines whether the sample urine has concentration of contents too high, in other words, the present invention determines whether more water intake is needed for the user. When the display unit 80 receives the detection result signal as displaying orange light, the display unit 80 accordingly displays the orange light, signaling the user to drink more water.

Figure 16:
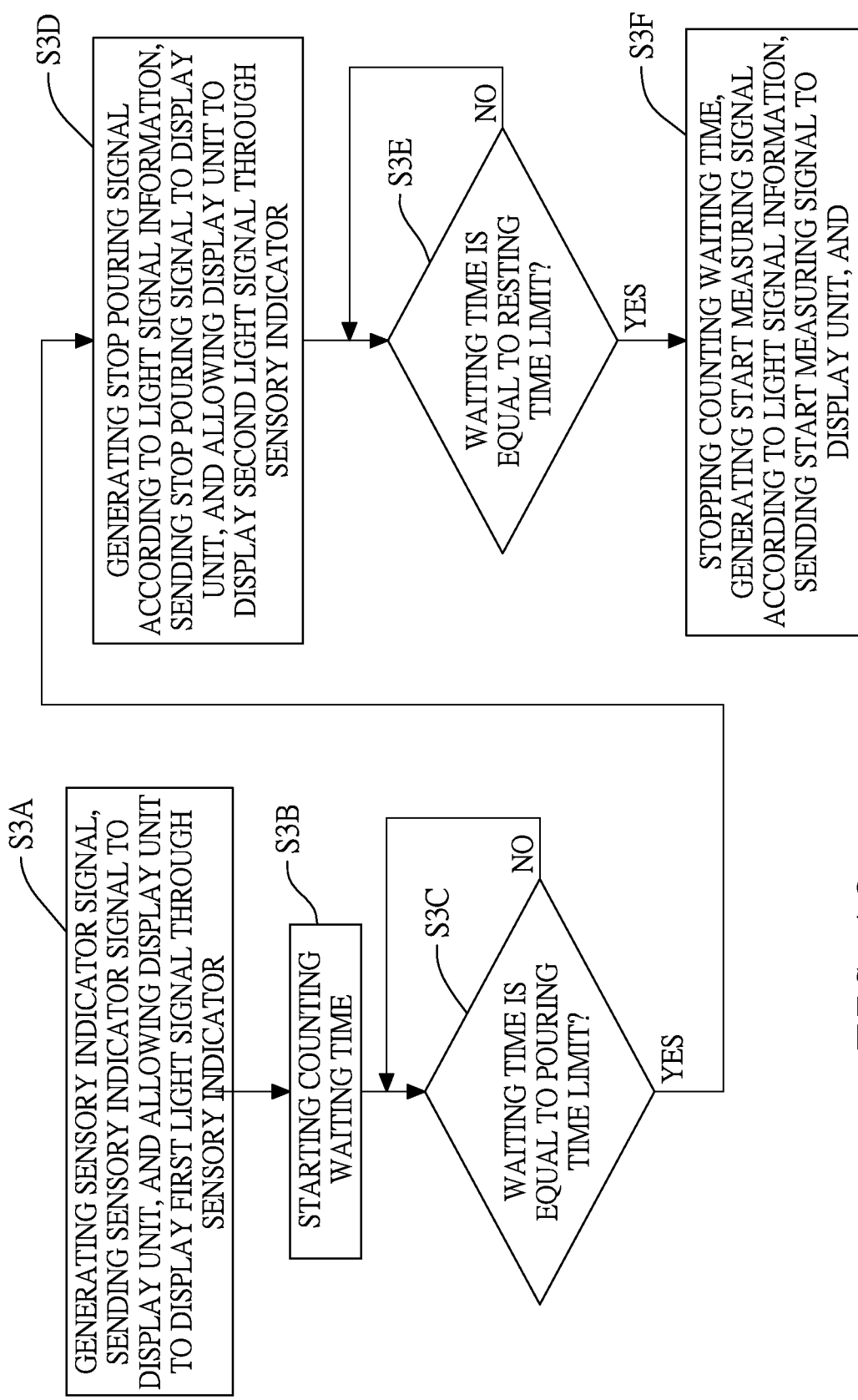
FIG. 16 is another flow chart of how another embodiment of the urinal additional device for detecting blood in urine functions.

With reference to FIG. 16, in another embodiment of the present invention, between steps S3 and S31, the method further includes the following sub-steps:

Step S3A: generating the sensory indicator signal, sending the sensory indicator signal to the display unit 80, and allowing the display unit 80 to display the first light signal through the sensory indicator 83.

Step S3B: starting counting the waiting time.

Step S3C: determining whether the waiting time is equal to the pouring time limit.

When determining the waiting time is yet to equal to the pouring time limit, continuing counting and re-executing step S3C.

Step S3D: When determining the waiting time is equal to the pouring time limit, generating the stop pouring signal according to the light signal information, sending the stop pouring signal to the display unit 80, and allowing the display unit 80 to display the second light signal through the sensory indicator 83.

Step S3E: further determining whether the waiting time is equal to the resting time limit.

When determining the waiting time is yet to equal to the resting time limit, continuing counting and re-executing step S3E.

Step S3F: When determining the waiting time is equal to the resting time limit, stopping counting the waiting time, generating the start measuring signal according to the light signal information, sending the start measuring signal to the display unit 80, and allowing the display unit 80 to display the third light signal through the sensory indicator 83.

Figure 17:
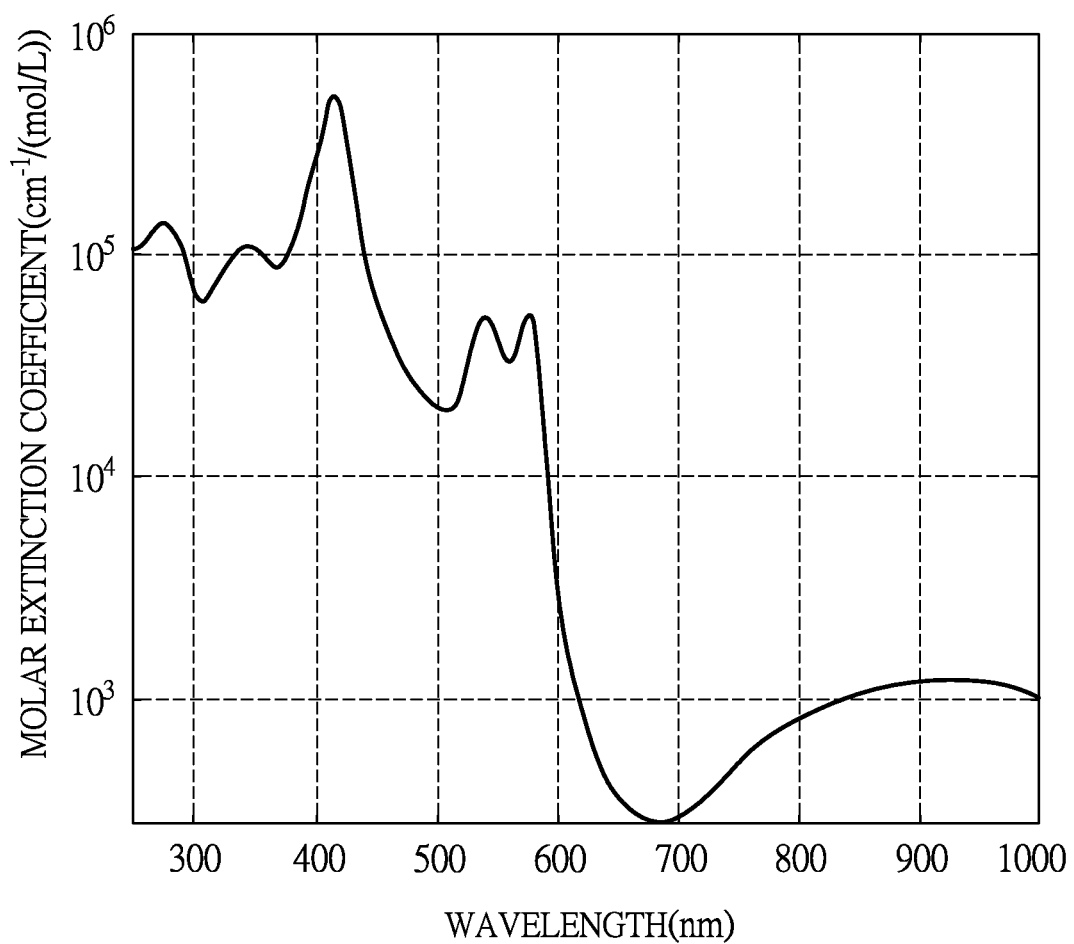
FIG. 17 is a perspective view of an absorption spectrum for blood.

With reference to FIG. 17, FIG. 17 is a perspective view of an absorption spectrum for blood. The absorption spectrum for blood includes a molar extinction coefficient of oxyhemoglobin under different wavelengths. When determining whether blood is present in the sample urine, the present invention analyzes whether oxyhemoglobin is present, since human blood includes large amounts of oxyhemoglobin. The greater the molar extinction coefficient is, the easier light of the corresponding wavelength is absorbed, and vise versa, the lesser the molar extinction coefficient is, the harder light of the corresponding wavelength is absorbed. With reference to FIG. 17, for wavelengths around visual spectrum at around 400 nanometers (nm) to 500 nm, the molar extinction coefficient of oxyhemoglobin is greatest around 410 nm. For wavelengths around visual spectrum at around 600 nm to 800 nm, the molar extinction coefficient of oxyhemoglobin is the least around 690 nm. In fact, wavelength around 690 nm is equivalent to wavelength of red light, and wavelength around 410 nm is equivalent to wavelength of purple light. With regard to the above description, oxyhemoglobin most easily absorbs purple light, and least absorbs red light. For this reason, when red light is least absorbed by oxyhemoglobin, red light is reflected and blood appears to be red.

The processing unit 40 of the present invention compares the spectrum information and the detection beam information. When the spectrum information and the detection beam information are similar, and when the spectrum information revels that purple light around 410 nm is yet to be absorbed in large quantity and red light around 690 nm is yet to reflect in large quantity, then the processing unit 40 determines blood is absent in the sample urine. On the other hand, when the spectrum information and the detection beam information are different, and when the spectrum information revels that purple light around 410 nm is absorbed in large quantity and red light around 690 nm is reflected in large quantity, then the processing unit 40 determines blood is present in the sample urine.

In another embodiment of the present invention, although absorption spectrum for water has noticeable wavelength characteristics outside of the visual spectrum, hence water appears to be transparent, water still affects concentration of contents of the sample urine. In other words, water affects the molar extinction coefficient of the spectrum information obtained by the processing unit 40. When the concentration of contents of the sample urine is high, the molar extinction coefficient of the spectrum information will be greater, and vice versa. This is how the processing unit 40 is able to determine whether water is present enough in the sample urine, and therefore further determines whether the user needs to replenish more water to dilute concentration of contents in the sample urine.

What is claimed is:

1. A urinal additional device for detecting blood in urine, comprising:
   a shell, comprising an entry hole and an exit hole; wherein the entry hole is formed on a side surface of the shell, and the exit hole is formed on another side surface of the shell;
   a flow pathway, formed within the shell and between the entry hole and the exit hole for communicating with the entry hole and the exit hole; wherein the flow pathway comprises a groove;
   a display unit, mounted on the shell;
   a measuring module, mounted inside the shell, comprising a first side and a second side; wherein the second side is opposite to the first side; and wherein the first side comprises a light emitting unit and a light sensing unit, and the second side comprises a lens; wherein the lens is mounted inside the groove;
   a holder, attached to the second side of the measuring module, and comprising a reflective mirror; wherein the reflective mirror is mounted on the holder parallel to the lens; and
   a processing unit, mounted within the shell, electrically connected to the measuring module and the display unit;
   wherein when a sample urine enters through the entry hole, flows through the flow pathway, and exits from the exit hole, a part of the sample urine remains in the groove of the flow pathway as collected urine;
   wherein the light emitting unit generates a detection beam toward the lens; the detection beam passes through the lens, passes through the collected urine, and shoots into the reflective mirror; once reflected by the reflective mirror, the detection beam passes through the lens and shoots into the light sensing unit, and the light sensing unit correspondingly generates a sensing signal; and
   wherein when the processing unit receives the sensing signal, the processing unit generates a detection result signal according to the sensing signal, sends the detection result signal to the display unit, and through the display unit displays a test result of the sample urine.

2. The urinal additional device for detecting blood in urine as claimed in claim 1, wherein:
   the processing unit further stores a detection beam information and a light signal information;
   the processing unit analyzes a spectrum information of the sensing signal, generates a detection result data according to the spectrum information and the detection beam information, and generates the detection result signal according to the detection result data and the light signal information;
   the display unit further comprises a result indicator; and
   the result indicator displays at least two colors of light according to the detection result signal in order to display the test result of the sample urine.

3. The urinal additional device for detecting blood in urine as claimed in claim 1, further comprising:
   a power unit, electrically connected to the processing unit, and supplies electricity to the processing unit; wherein:
   the display unit further comprises a low power indicator;
   the processing unit stores an internal data, and the internal data comprises a low power threshold value; and
   when the processing unit detects a remaining power of the power unit is less than the low power threshold value, the processing unit generates a low on power signal, sends the low on power signal to the display unit, and through the display unit lights up the low power indictor.

4. The urinal additional device for detecting blood in urine as claimed in claim 1, further comprising:
   a heat sensory unit, mounted inside the flow pathway, and electrically connected to the processing unit; wherein:
   the processing unit stores an internal data, and the internal data comprises a thermistor threshold value; and
   when the processing unit determines a resistance value of the heat sensory unit is less than or equal to the thermistor threshold value, only then the processing unit starts controlling the light emitting unit to generate the detection beam.

5. The urinal additional device for detecting blood in urine as claimed in claim 4, wherein:
   the processing unit further stores a light signal information, and the light signal information comprises a first light signal;

the display module further comprises a sensory indicator; and when the processing unit determines the resistance value of the heat sensory unit is less than or equal to the thermistor threshold value, the processing unit generates a sensory indicator signal according to the light signal information, sends the sensory indicator signal to the display unit, and through the display unit displays the first light signal through the sensory indicator.

6. The urinal additional device for detecting blood in urine as claimed in claim 5, wherein:

the processing unit further stores a pouring time information and a resting time information; the pouring time information comprises a pouring time limit, and the resting time information comprises a resting time limit;

the light signal information further comprises a second light signal and a third light signal;

when the processing unit generates the sensory indicator signal, the processing unit starts counting a waiting time;

when the waiting time equals the pouring time limit, the processing unit generates a stop pouring signal according to the light signal information, sends the stop pouring signal to the display unit, and through the display unit displays the second light signal through the sensory indicator;

when the waiting time equals the resting time limit, the processing unit stops counting the waiting time, generates a start measuring signal according to the light signal information, sends the start measuring signal to the display unit, and through the display unit displays the third light signal through the sensory indicator; and only after the processing unit starts generating the start measuring signal, the processing unit starts controlling the light emitting unit to generate the detection beam.

7. The urinal additional device for detecting blood in urine as claimed in claim 1, wherein:

the measuring module further includes an emitting light optical channel and at least one reflected light optical channel; the emitting light optical channel and the at least one reflected light optical channel are located between the first side and the second side;

the detection beam emitted from the light emitting unit travels to the lens through the emitting light optical channel; and after reflected by the reflection mirror, the detection beam passes the lens and travels to the light sensing unit through the at least one reflected light optical channel.

8. The urinal additional device for detecting blood in urine as claimed in claim 7, wherein:

the emitting light optical channel is formed at a center of the measuring module, and the at least one reflected light optical channel is formed outside of the emitting light optical channel; and a first distance between the at least one reflected light optical channel and the emitting light optical channel on the first side is greater than a second distance between the at least one reflected light optical channel and the emitting light optical channel on the second side.

9. The urinal additional device for detecting blood in urine as claimed in claim 1, wherein:

the shell comprises a first shell, a second shell, and a third shell;

the first shell comprises a chute, the entry hole, the flow pathway, and a first space;

the second shell is mounted on a side of the first shell; the side comprises the first space; the second shell comprises a second space, and the second space communicates with the first space;

the measuring module is mounted inside the first space and the second space;

the entry hole is formed on a top surface of the first shell, and the chute is formed beside the entry hole; the chute tilts from the top surface of the first shell towards the flowing channel;

the third shell is mounted on a bottom surface of the first shell, and the third shell comprises the exit hole and a third space; the third space communicates with the flow pathway of the first shell; and the third space of the third shell comprises the groove of the flow pathway.

10. The urinal additional device for detecting blood in urine as claimed in claim 1, further comprising:

a drain hole, formed on a bottom wall of the groove of the flow pathway; wherein the drain hole further forms through the bottom wall of the groove and an under surface of the shell.

11. The urinal additional device for detecting blood in urine as claimed in claim 2, further comprising:

a drain hole, formed on a bottom wall of the groove of the flow pathway; wherein the drain hole further forms through the bottom wall of the groove and an under surface of the shell.

12. The urinal additional device for detecting blood in urine as claimed in claim 3, further comprising:

a drain hole, formed on a bottom wall of the groove of the flow pathway; wherein the drain hole further forms through the bottom wall of the groove and an under surface of the shell.

13. The urinal additional device for detecting blood in urine as claimed in claim 4, further comprising:

a drain hole, formed on a bottom wall of the groove of the flow pathway; wherein the drain hole further forms through the bottom wall of the groove and an under surface of the shell.

14. The urinal additional device for detecting blood in urine as claimed in claim 5, further comprising:

a drain hole, formed on a bottom wall of the groove of the flow pathway; wherein the drain hole further forms through the bottom wall of the groove and an under surface of the shell.

15. The urinal additional device for detecting blood in urine as claimed in claim 6, further comprising:

a drain hole, formed on a bottom wall of the groove of the flow pathway; wherein the drain hole further forms through the bottom wall of the groove and an under surface of the shell.

16. The urinal additional device for detecting blood in urine as claimed in claim 7, further comprising:

a drain hole, formed on a bottom wall of the groove of the flow pathway; wherein the drain hole further forms through the bottom wall of the groove and an under surface of the shell.

17. The urinal additional device for detecting blood in urine as claimed in claim 8, further comprising:

a drain hole, formed on a bottom wall of the groove of the flow pathway; wherein the drain hole further forms through the bottom wall of the groove and an under surface of the shell.

* * * * *